(12) United States Patent
Zoccatelli

(10) Patent No.: US 9,427,197 B2
(45) Date of Patent: Aug. 30, 2016

(54) METHOD AND APPARATUS TO GENERATE A PANORAMIC RADIOGRAPHY

(71) Applicant: QR Srl, Imola (IT)

(72) Inventor: Giacomo Zoccatelli, Negrar (IT)

(73) Assignee: QR S.r.l. (IT)

( * ) Notice: Subject to any disclaimer, the term of this patent is extended or adjusted under 35 U.S.C. 154(b) by 115 days.

(21) Appl. No.: 14/444,226

(22) Filed: Jul. 28, 2014

(65) Prior Publication Data

US 2015/0036790 A1   Feb. 5, 2015

(30) Foreign Application Priority Data

Jul. 31, 2013   (IT) .............................. BO2013A0422

(51) Int. Cl.
*A61B 6/00* (2006.01)
*G06T 7/00* (2006.01)
*A61B 6/14* (2006.01)
(Continued)

(52) U.S. Cl.
CPC . *A61B 6/14* (2013.01); *A61B 6/03* (2013.01); *G06T 3/0031* (2013.01); *G06T 11/006* (2013.01)

(58) Field of Classification Search
CPC ......... A61B 6/14; A61B 6/03; G06T 11/006; G06T 3/0031
See application file for complete search history.

(56) References Cited

U.S. PATENT DOCUMENTS 8,325,874 B2   12/2012   Shi et al.
2005/0237324 A1   10/2005   Guhring
(Continued)

FOREIGN PATENT DOCUMENTS

EP   1973075 A1   9/2008
EP   2223653 A1   9/2010
EP   2254475 B1   8/2011

OTHER PUBLICATIONS

Akhoondali, et al, "Fully Automatic Extraction of Panoramic Dental Images from CT-Scan Volumetric Data of the Head," Journal of Applied Sciences, 2009, pp. 2106-2114, 9:11, Asian Network for Scientific Information.
(Continued)

*Primary Examiner* — David J Makiya
*Assistant Examiner* — Dani Fox
(74) *Attorney, Agent, or Firm* — Laubscher, Spendlove & Laubscher, P.C.

(57) ABSTRACT

A method for obtaining a panoramic image similar to a panoramic radiography obtained from a patient through X-ray emission by processing an acquired 3D digital volume in voxel, each voxel having values of X-ray absorption is characterized by selecting a curved surface in 3D volume and identifying a plurality of first points on the curved surface and connecting each point of the identified first points with a corresponding pixel of the panoramic image to be obtained in order to map the first points of the curved surface on corresponding pixels of the panoramic image. Each identified point of the first points are associated with a respective set of lines passing through the identified point, each line having a different angle of incidence. The lines are contained in a solid angle having identified point as a vertex. An absorption value is calculated in the 3D volume along each of the lines. The identified point of the first points is attributed with an absorption value calculated as a function of all of the absorption values calculated for each of the lines of the set. The pixel linked to the identified point of the first points is attributed with a value expressed in grayscale calculated as a function of the absorption value of the identified point.

12 Claims, 3 Drawing Sheets

(51) Int. Cl.
*A61B 6/03* (2006.01)
*G06T 3/00* (2006.01)
*G06T 11/00* (2006.01)

(56) References Cited

U.S. PATENT DOCUMENTS

| | | | |
|---|---|---|---|
| 2008/0232539 A1* | 9/2008 | Pasini | A61B 6/032 378/4 |
| 2011/0026671 A1* | 2/2011 | Shi | A61B 6/14 378/39 |
| 2011/0033026 A1 | 2/2011 | Ulrici et al. | |

OTHER PUBLICATIONS

Bing, et al, "An Automatic Method of Synthesizing Panoramic Radiography by Unwrapping Dental CT Image," International Conference on Mechatronic Science, Electric Engineering and Computer, Aug. 19-22, 2011, pp. 1094-1096, IEEE, Jilin, China.

Tohnak, et al, "Synthesizing Panoramic Radiographs by Unwrapping Dental CT Data," Proceedings of the 28th IEEE EMBS Annual International Conference, Aug. 30, 2006-Sep. 1, 2006, pp. 3329-3332, IEEE, New York, NY.

Tahnak, et al, "Synthesizing Dental Radiographs for Human Identification," Journal of Dental Research, 2007, pp. 1057-1062, 86:11.

* cited by examiner

METHOD AND APPARATUS TO GENERATE A PANORAMIC RADIOGRAPHY

CROSS REFERENCE TO RELATED APPLICATION

This application is a new U.S. Utility application claiming priority benefit of IT BO2013A000422, filed Jul. 31, 2013, the entire contents of which are hereby incorporated by reference.

The invention relates to a method and an apparatus for extraoral dental radiography, suitable for generating tomographic images similar, for their features, to a panoramic tomographic radiographic image (in the following, panoramic image). In particular, the invention relates to a method to obtain a panoramic image similar to that of a panoramic radiography obtained through X-rays, the method processing a 3D digital volume in voxel obtainable through computerized tomography (CT).

Each voxel, in the 3D volume, has a respective scalar value indicating an X-ray absorption, which is directly correlated to the density of the material through which the X-ray themselves passed. Usually the value of each voxel in a 3D volume is represented in a grayscale image.

BACKGROUND OF THE INVENTION

Panoramic radiographic images, sometimes also known as orthopantomographies, are well known in the dental field: they are two-dimensional radiographic images of a predefined curved plan approximating patient jaws; such image identifies a limited layer where anatomical structures are focused, outside which anatomical structures are blurred.

The main characteristics of a panoramic image are:
the thickness of the blurred area around the focused layer;
the acquisition angle, that is the angle defined between a direction of acquisition and a direction orthogonal to focused layer.

These characteristics vary from pixel to pixel of the panoramic image itself.

A panoramic image is normally produced using a known specific panoramic apparatus, similar to that described e.g. in the Spartiotis EP2223653 patent, which exposes a patient's head to the X-rays emitted by an X-ray emitter. The rays are received by an X-ray sensor, provided with a matrix of receivers (or pixels) of few columns in width, which is opposed to the emitter. The sensor forms a partial radiographic image of the patient's head exposed to X-rays.

Moving the X-ray transmitter and receiver along a predefined trajectory, the complete panoramic image is produced acquiring a plurality of the partial radiographic images along the trajectory, and summing the partial images, which are superimposed and horizontally shifted by a suitable distance.

Alternatively, producing a panoramic image, which is per se a two-dimensional image, is also possible by processing 3D volumetric data obtained with a CBCT (Cone Beam Computerized Tomography) apparatus.

In this case a sensor having few columns in width is simulated, through which the partial image is acquired. The same acquisition method is virtually repeated, shifting the X-ray sensor and emitter on the predefined trajectory used in the above-described panoramic apparatus. The difference lies in the fact that each partial image is virtually calculated starting from 3D volumetric data expressed as voxels.

Such a method is known from the Ulrici, et al EP 2254475 patent, where a tomographic blurring method of an orthopantomograph is simulated. The panoramic image is calculated from the 3D volume previously acquired, corresponding each point of the panoramic image to a voxel of the 3D acquired volume which is selected as focused.

A problem of the panoramic images acquired both through a panoramic apparatus and through simulation starting from a 3D volume as in the Ulrici et al patent EP 2254475 arises from the fact that the panoramic image to be acquired lies on a curve.

From this the fact that in each partial image acquired by the (real or virtual) receiving sensor is only a column, typically the central column of such sensor, the sensor will correctly focus the desired point on that curve which follows. The other columns will have a positioning error which, when the sum of partial images is performed, leads to a slight blurring even in the curve itself which is to be focused.

Another problem is that the main features of an obtained panoramic image are connected, for each pixel, to those of the adjacent pixels, in that partial images are summed up superimposed to each other.

An alternative method to process 3D volumetric data to obtain a two-dimensional image "similar" to a panoramic image, as will be explained in the following, is known from the Pasini EP1973075 patent and Imaging Sciences International the Shi, et al U.S. Pat. No. 8,325,874.

The Pasini EP1973075 patent describes a processing method which extracts a layer of a 3D volume, having a defined thickness, laying between two different curves, one more internal and one more external to patient's head, and calculates an absorption in a direction orthogonal to a curve which is central between the external and the internal curve. According to this processing method there is no blurring, and therefore the two-dimensional image obtainable is "similar" to a panoramic image, in the sense that the image is "cleaner" with respect to a traditional panoramic image, in that some anatomical structures are not visible.

SUMMARY OF THE INVENTION

This is a problem, since medical operators are not familiar with a two-dimensional image without such anatomical structures, and prefer a traditional panoramic image.

The present invention aims to provide a processing method and apparatus for obtaining 2D panoramic images starting from 3D acquisitions, having an improved accuracy.

BRIEF DESCRIPTION OF THE DRAWINGS

Further advantages and features of the present invention are described in the following, wherein exemplary embodiments are explained in detail on the basis of the drawings.

DETAILED DESCRIPTION OF THE INVENTION

Figure 1:
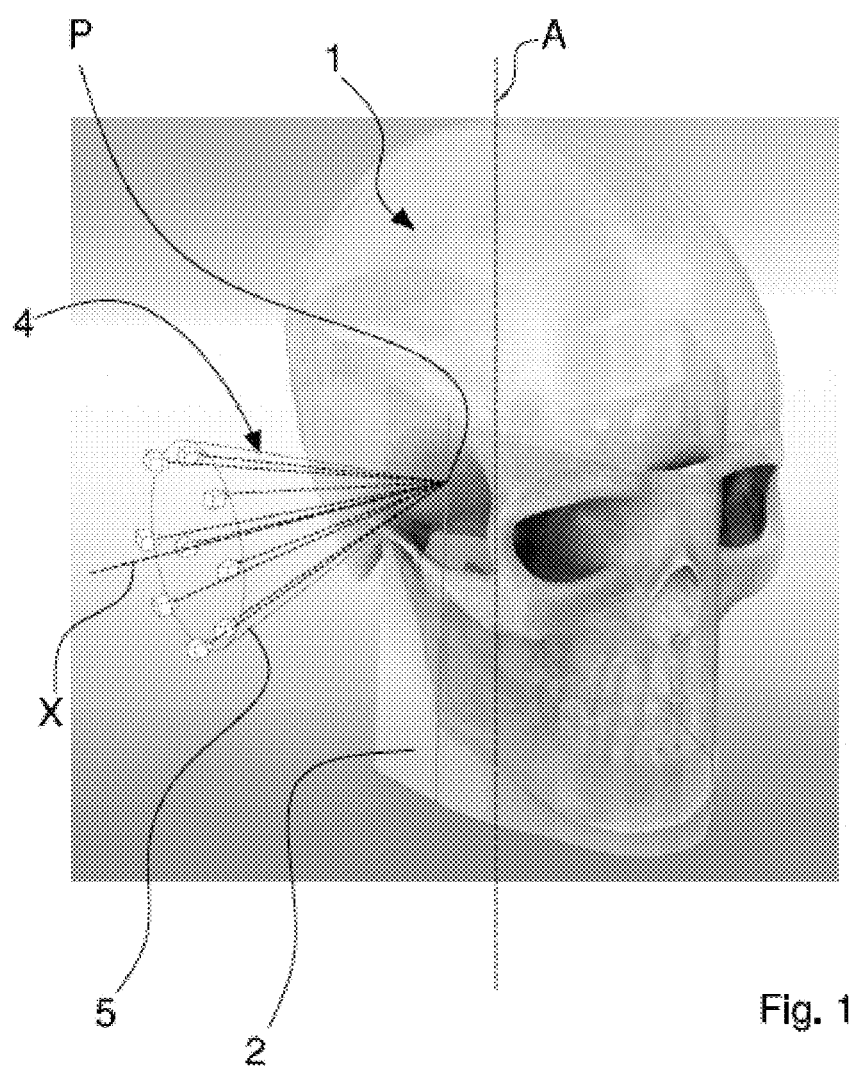
FIG. 1 shows a 3D volume acquired through a Cone Beam Computerized Tomography (CBCT); a curved surface is selected in such 3D volume, which will be the focused surface of the panoramic image, wherein an identified point P in such curved surface is shown, together with a set of lines passing through the point each having a different angle of incidence, contained in a solid angle having the point as its vertex.

With reference to FIG. 1, 1 indicates a 3D digital volume expressed in voxel which was acquired through CBCT (Cone-Beam Computerized Tomography).

Each voxel has a respective X-ray absorption value expressed by a scalar number, which is visualized in FIG. 1 as grayscale. It is pointed out that a similar 3D volume 1 might be acquired through a technique different from CBCT, e.g. through fan-beam computerized axial tomography (CAT).

An apparatus (not illustrated) is provided to process the 3D digital volume 1 in voxel, so as to obtain a panoramic image similar to a panoramic image directly obtained from a patient through X-ray emission.

The apparatus includes a processing unit, and optionally a device for acquiring 3D volume 1, which in the above-mentioned case may be of the CBCT or CAT type.

Figure 3:
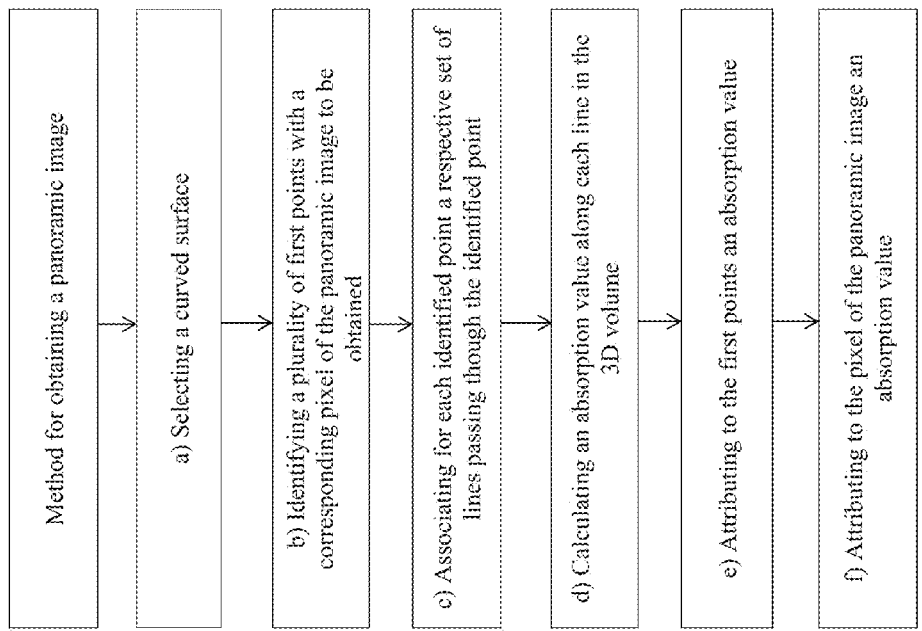
FIG. 3 shows a schematic illustrating the interaction between the processing unit and an apparatus suitable for processing a 3D volume.
Figure 3:
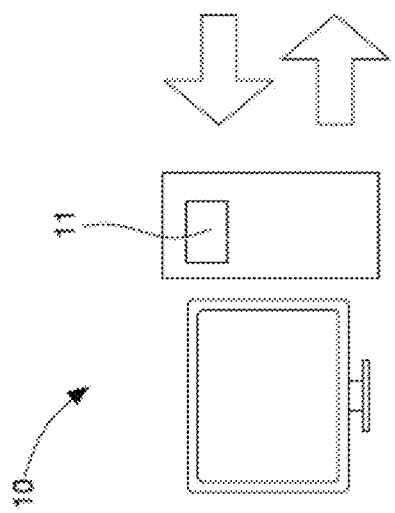

In other words, the apparatus may include both the device for acquiring a 3D volume, and the processing unit to process the 3D volume 1 directly acquired. Alternatively, with reference to FIG. 3, the apparatus 10 may be provided with the processing unit 11 only, inasmuch as the 3D volume 1 to be processed was previously acquired. In this last case, the processing unit 11 might be positioned even at a large distance from the device for acquiring the 3D volume 1.

In use, the processing unit of the apparatus performs a processing method according to the present invention, allowing a panoramic image similar to that of a panoramic radiography obtained directly from a patient through X-ray emission to be obtained.

The method of the present invention includes a step a) of selecting a curved surface 2 in the 3D volume 1.

To select such curved surface 2, a human operator may perform a selection through a suitable graphic interface, and/or an automatic selection of such curved surface 2 may be provided through an algorithm searching for characteristic anatomic structures, and/or a predefined form of curved surface 2 may be provided.

All of the above-indicated possibilities of selection may also be combined in a suitable manner, e.g. through an operator interface, an operator may modify a predefined shape of the curved surface 2, and/or a shape defined by automatic search algorithm.

Moreover, before step a) of selection of the curved surface 2, undesired anatomic structures may be optionally removed from the acquired 3D volume 1 in order to simplify the 3D volume 1 for its successive processing.

After selecting the curved surface 2, the method includes the step b) of identifying a plurality of first points 3 on the curved surface 2 (FIG. 2) and connecting each point P of the identified first points 3 with a corresponding pixel of the panoramic image to be obtained, so as to map the first points 3 of the curved surface 2 on corresponding pixels of the panoramic image to be obtained.

By way of illustration only, the curved surface 2 of FIG. 1 has a height of about 1,500 points and a width of 3,000 points. With the present method, 1,500×3,000=4,500,000 points of the curved surface 2 on corresponding pixels of the panoramic image to be obtained must be mapped.

The method further includes the step c) of associating, for each identified point P of the plurality of first points 3, a respective set of lines 4 passing through the identified point P, each line having a different angle of incidence, the lines being contained in a respective solid angle 5 having the identified point P as vertex. For each line, the respective angle of incidence is defined as the angle between the line and a line X perpendicular to the curved surface 2 passing through the identified point P.

To vary the quality characteristics of the panoramic image point by point, or in specific portions, the number of lines of the set 4 and a specific angle for each line can be selected for each identified point P or for determined areas of the curved surface 2.

For instance, a distribution of lines of the set of lines 4 in the solid angle 5 determines a depth of field of the panoramic image, which is inversely proportional to the width of such distribution.

This improves the overall quality of the obtained panoramic image, in that greater flexibility is allowed in processing the image itself. The possibility of varying point-by-point on the curved surface the number of lines of set of lines 4, their angle of incidence, and optionally also the distribution thereof, allows the curved surface 2 in correspondence of the transition area between the front area and the canine teeth area to be processed in a different way from that of the remaining lateral molar teeth areas. The transition area here is strongly curved and therefore requires a different attention with respect to the premolar-molar area or of the incisors.

The portions of panoramic image corresponding to such areas of the curved surface will then have characteristics of different quality.

The method further includes the step d) of calculating an absorption value along each said line in the 3D volume, e.g. inside the 3D volume, and the step e) of attributing to the identified point P of the first points 3 an absorption value, calculated as a function of the absorption values calculated for each line of the set of lines 4 in the solid angle 5 associated to the identified point P.

The method further includes the step f) of attributing to the pixel of the panoramic image connected to the identified point P of the first points 3 a value expressed in grayscale, which is calculated as a function of the absorption value of the identified point P.

For instance, as the absorption value is a scalar number graphically represented in an axial tomographic image with grayscale, in the same way the pixel value of the panoramic image can assume the same scalar of the calculated absorption value, or can assume a different value, for instance proportional, but not identical, to the absorption value.

As set forth above, in step d) of the method, for each line of the set of lines 4 an absorption in the 3D volume is calculated.

For calculating such absorption, first of all for each line a set of second points (not illustrated) in the 3D volume is selected in a step d1). Indeed, each line passes through the identified point P and extends also in the 3D volume, defined by voxels.

Given a specific line, for each selected point of the second points in the 3D volume, the voxels surrounding the selected points are separated in a step d2). In a step d3), a weighted average of the absorption value of such surrounding voxels is further calculated, and to the selected point of the second points of the line in a step d4) an absorption value equal to such weighted average is attributed.

The absorption values calculated for each selected point of the second points of the specific line are summed together, giving them a weight dependent on the distance of the identified point P identifying a layer to be focused, and the sum is attributed to such line as absorption value in the 3D volume.

The weighted average, calculated in the step d3), is obtained evaluating the distance of the selected point of the second points with respect to the center of the voxels surrounding the point itself.

In detail, for each of the surrounding voxels presenting a respective center, the respective absorption value corresponding to the center is considered, and a distance between the center and the selected point of such second points is evaluated.

The weighted average is obtained summing each absorption value of each voxel, multiplied by a coefficient which is a function of the distance of the voxel centre to the selected point of such second points.

In this way, each point of the set of second points of the line has an absorption value taking into account the position of the point itself in the 3D volume, that is the arrangement of the point with respect to the voxels of the 3D volume surrounding it.

Once the absorption along each line in the 3D volume was calculated, we said that the method calculates in step e) the absorption in the point P of the first set of points 3 of the curved surface 2 as a function of all the absorptions calculated for each line.

In particular, such step e) includes calculating a weighted average of the absorption values of the lines of the set of lines 4.

As set forth above, each line is characterized by an angle of incidence, previously defined with respect to the perpendicular line X. To calculate the weighted average, the absorption values of each line are summed together and each absorption value is multiplied by a coefficient which is a function of the angle of incidence of the line itself.

This allows greater coefficients to attribute to lines having small angles of incidence with respect to lines having bigger angles of incidence, to privilege the substantially null angles of incidence, that is acquisitions orthogonal to the curved surface 2 of 3D volume.

As set forth above, step b) includes identifying a plurality of first points 3 on the curved surface 2, and the calculating method of the present invention is based on processing performed for each point P of such first points 3.

To identify such first points 3 on the curved surface 2, sections of the curved surface 2 are made with surfaces predefined in a step b1), and intersection lines 6 between the curved surface 2 and such predefined surfaces are obtained in a step b2). The first points 3 are identified in the intersection lines 6 so defined.

The shape of these predefined surfaces can be planar or curved, and this shape may be selected as curved when possible distortions to the image are to be applied, or as a function of the characteristics of quality of the panoramic image to be obtained.

Considering a longitudinal axis A in the 3D volume, making the sections in such volume as in step b1) is possible, using parallel planes orthogonal to such longitudinal axis A, to obtain therefore axial sections of the 3D volume.

The points identified among the plurality of first points 3 in the intersection lines 6 can be chosen equidistant to each other, or with a variable distance, this variable distance conveniently chosen as a function of the characteristics of quality of the panoramic image to be obtained.

Figure 2:
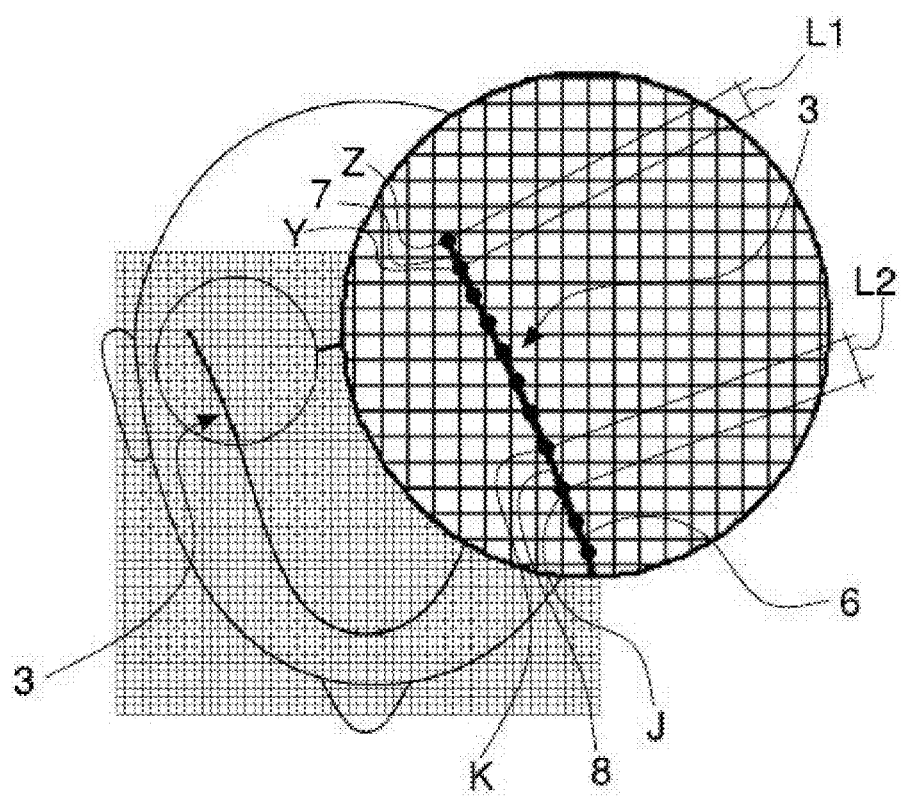
FIG. 2 shows a top schematic illustration of an axial section of the image of FIG. 1, immersed in a grid representing a plurality of voxels. The figure shows the selected curved surface, a plurality of first points identified in that curved surface, and also a magnification of a portion of the curved surface with the identified first points.

FIG. 2 shows an intersection line 6 obtained through an axial section, and some of the points identified as a plurality of first points 3 are shown by way of example. If we consider two consecutive points identified as Z and Y, which are ends of a first section 7 of the intersection line 6, and two further consecutive points K and J, which are ends of a second section 8 of such line 6, the fact that the first section 7 has a length L1 shorter than L2, which is the length of the second section 8, can be observed. The distance between the points Z and Y is therefore shorter than the distance between the points K and J, and this depends on an average angle of observation with which the curved surface 2 has to be framed, at the first section 7 or at the second section 8.

According to an embodiment of the present invention, the curved surface 2 to be analyzed in the 3D volume includes generating lines, parallel to each other, which are moreover parallel to the longitudinal axis of 3D volume. In other words, given any curved line in an axial section of the 3D volume, the curved surface 2 through which the panoramic image is mapped is the one projected from such curved line according to the direction normal to the section plan itself.

In this specific case, the creation of the panoramic image can proceed considering all the points laying on one of such projection segments, that is on a column. All the points identified of the same column of the curved surface 2 will therefore be associated to the corresponding pixels of the panoramic image, and for each point lines having different angles will be considered, but contained in a planar angle having a determined width.

According to this embodiment, the processing method is less onerous, from the point of view of calculation.

In addition to the method, a program is further provided, including code to implement a method to obtain a panoramic image similar to that of a panoramic image obtained through X-rays, wherein the method processes a 3D digital volume, as set forth above, and wherein the program is performed in an apparatus as described above.

With the present invention, an improved panoramic image can be obtained, in that for each point P of the curved surface 2 an absorption in the 3D volume is calculated, separately and independently of the remaining points. Moreover, for each identified point P, or for predefined zones of the curved surface, the processing parameters of 3D volume can be varied, so allowing a high flexibility of acquisition of the anatomic structures themselves.

Finally, the panoramic image being processed starting from the voxel of the 3D volume and not only from the voxel of one of its layers, the panoramic image so obtained is familiar to the medical operators to whom it is intended.

The calculation of the absorption along the set of lines overlooks the constraints imposed by an X-ray emitter and receiver having defined dimensions, mobile on a predefined trajectory. The acquisition is no more constrained to those dimensions, thus the panoramic image is improved.

What is claimed is:

1. A method for obtaining a panoramic image similar to a panoramic radiography obtained from a patient through X-ray emission by processing an acquired 3D digital volume in voxel, each voxel having values of X-ray absorption, the method comprising the steps of
   a) selecting a curved surface in 3D volume;
   b) identifying a plurality of first points on said curved surface and connecting each point of said plurality of first points with a corresponding pixel of the panoramic image to be obtained to map said plurality of first points on said curved surface to each corresponding pixel of said panoramic image;
   c) associating, for each identified point of said plurality of first points, a respective set of lines passing through the identified point, each line of the respective set of lines having a different angle of incidence, the angle of incidence defined as an angle between a line of the respective set of lines and a line perpendicular to the curved surface passing through the identified point, each line of the respective set of lines being contained in a solid angle having the identified point as the vertex of the solid angle;

d) calculating an absorption value in the 3D volume along each line;

e) attributing, to each identified point, an absorption value calculated as a function of all of the absorption values calculated for each line of the respective set of lines; and f) attributing, to each corresponding pixel linked to each identified point, a value expressed in grayscale calculated as a function of the absorption value of each identified point.

2. A method according to claim 1, wherein said step of associating a respective set of lines comprises selecting, for each identified point and/or for determined areas of said curved surface, a predetermined number of lines of said respective set of lines and a specific angle of incidence for each line to vary the quality features of said panoramic image.

3. A method according to claim 1, wherein said step of calculating an absorption value in the 3D volume comprises the steps of d1) selecting a set of second points along each line of the respective set of lines;

d2) for each selected point of said second points, identifying voxels surrounding each selected point;

d3) calculating a weighted average of absorption values of said surrounding voxels;

d4) attributing to each selected point an averaged absorption value equal to said weighted average; and d5) calculating a sum by summing all of the averaged absorption values calculated for each selected point along each corresponding line, wherein each averaged absorption value for each second point is assigned a weight dependent upon a distance from each second point to the corresponding identified point defining the vertex of each line, and attributing said sum to said each corresponding line as the absorption value in the 3D volume.

4. A method according to claim 3, wherein said step of calculating a weighted average of the absorption value of said surrounding voxels comprises for each of said surrounding voxels having a respective center, considering the respective absorption value corresponding with said center;

evaluating a respective distance between said center and said selected point of said set of second points; and summing each absorption value for each voxel of said surrounding voxels, multiplied by a coefficient function of said respective distance.

5. A method according to claim 1, wherein said step of attributing to each identified point an absorption value comprises calculating a weighted average of the absorption values of each line.

6. A method according to claim 5, wherein said step of calculating said weighted average comprises summing said absorption value of each line, multiplied by a coefficient function of said angle of incidence.

7. A method according to claim 1, wherein said step of selecting a curved surface in 3D volume comprises
allowing a human operator to perform said selection through a suitable graphic interface; and/or
automatically selecting said curved surface through an algorithm searching for characteristic anatomical features; and/or
using a predefined shape of said curved surface.

8. A method according to claim 1, wherein said step of identifying a plurality of said first points on said curved surface comprises
b1) making sections of said curved surface with predefined surfaces; and
b2) obtaining intersection lines between said curved surface and said predefined surfaces and identifying said plurality of first points in said intersection lines.

9. A method according to claim 8, wherein said 3D volume has a longitudinal axis and wherein said step of making said sections comprises using parallel planes orthogonal to said longitudinal axis to obtain axial sections of said 3D volume.

10. A method according to claim 8, wherein said step of identifying said plurality of first points in said intersection lines comprises selecting points equidistant to each other, or selecting points at a variable distance, said variable distance being a function of quality of the panoramic image to be obtained.

11. A method according to claim 1, and further comprising the step of removing undesired anatomic structures from said 3D volume before said step of selecting a curved surface in said 3D volume.

12. A non-transitory computer readable medium embodying a program comprising code to implement a method to obtain a panoramic image similar to that of a panoramic image obtained through X-rays, processing a digital 3D volume acquired by means of a method according to claim 1, when said program is performed by a processing unit to process said 3D volume.

* * * * *